US012653930B2

(12) United States Patent
Ke et al.

(10) Patent No.: US 12,653,930 B2
(45) Date of Patent: Jun. 16, 2026

(54) ALVEOLAR BONE AUGMENTATION SCAFFOLD SYSTEM

(71) Applicant: NOVAPRINT THERAPEUTICS SUZHOU CO., LTD., Suzhou (CN)

(72) Inventors: Dongxu Ke, Suzhou (CN); Xi Yang, Suzhou (CN)

(73) Assignee: Novaprint Therapeutics Suzhou Co., Ltd, Jiangsu (CN)

( * ) Notice: Subject to any disclaimer, the term of this patent is extended or adjusted under 35 U.S.C. 154(b) by 734 days.

(21) Appl. No.: 18/081,938

(22) Filed: Dec. 15, 2022

(65) Prior Publication Data

US 2023/0119400 A1     Apr. 20, 2023

Related U.S. Application Data

(63) Continuation-in-part of application No. PCT/CN2021/129566, filed on Nov. 9, 2021.

(30) Foreign Application Priority Data

Nov. 13, 2020    (CN) .......................... 202011268945.3

(51) Int. Cl.
    *A61L 27/56*        (2006.01)
    *A61L 27/24*        (2006.01)
    *A61L 27/22*        (2006.01)
(52) U.S. Cl.
    CPC ............... *A61L 27/56* (2013.01); *A61L 27/24* (2013.01); *A61L 27/222* (2013.01)
(58) Field of Classification Search
    CPC ........ A61L 27/56; A61L 27/24; A61L 27/222; A61L 27/26; A61L 27/46; A61L 27/50;
    (Continued)

(56) References Cited

U.S. PATENT DOCUMENTS

| | | | | | |
|---|---|---|---|---|---|
| 6,165,486 | A | * | 12/2000 | Marra ..................... | A61L 27/46 |
| | | | | | 424/428 |
| 2005/0177118 | A1 | * | 8/2005 | Hoganson .............. | A61K 38/15 |
| | | | | | 623/1.42 |

(Continued)

FOREIGN PATENT DOCUMENTS

| | | |
|---|---|---|
| CN | 105228552 A | 1/2016 |
| CN | 105497981 A | 4/2016 |

(Continued)

OTHER PUBLICATIONS

CN-111904666-A Translation (Year: 2020).*
CN-107280787-A Translation (Year: 2017).*
CN-109646714-A Translation (Year: 2019).*

*Primary Examiner* — Sarah W Aleman
*Assistant Examiner* — Rebecca Lynee Zimmerman
(74) *Attorney, Agent, or Firm* — Thomas Ohman; Laine IP Oy

(57)     ABSTRACT

Provided is an alveolar bone augmentation scaffold system. The scaffold system includes the following structures: a porous augmentation scaffold fabricated by 3D printing using composite materials for filling alveolar bone defects; a mechanical separating plate, wrapped around the porous augmentation scaffold with a biomimetic structure for restoring alveolar bone defects; the augmentation scaffold is provided with a first region close to dental pulp, a second region away from the dental pulp, and a third region surrounding the second region, wherein pore diameters of three-dimensional porous structure of the above three regions are R1, R2, and R3 respectively, and they satisfy $R1 \geq R2 > R3$.

19 Claims, 3 Drawing Sheets

(58) Field of Classification Search
CPC ....... A61L 2430/12; B33Y 80/00; A61C 5/20;
A61C 8/0006; A61C 13/0019; A61F
2002/2835; A61F 2/2846; A61F 2/3099;
A61F 2/2803; A61F 2002/30784; A61B
17/8071
See application file for complete search history.

(56)                       References Cited

U.S. PATENT DOCUMENTS

| | | | |
|---|---|---|---|
| 2012/0101535 A1 | 4/2012 | Atkinson et al. | |
| 2017/0304056 A1* | 10/2017 | Gaignon | ................. A61L 27/58 |
| 2020/0085877 A1* | 3/2020 | Masoumi | ................. A61F 2/24 |

FOREIGN PATENT DOCUMENTS

| | | | | |
|---|---|---|---|---|
| CN | 106620882 A | | 5/2017 | |
| CN | 107280787 A | * | 10/2017 | ............ A61L 27/12 |
| CN | 107496982 A | | 12/2017 | |
| CN | 109646714 A | * | 4/2019 | ............ A61L 27/34 |
| CN | 109876184 A | | 6/2019 | |
| CN | 111110404 A | | 5/2020 | |
| CN | 111544139 A | | 8/2020 | |
| CN | 111545753 A | | 8/2020 | |
| CN | 211271408 U | | 8/2020 | |
| CN | 111839771 A | | 10/2020 | |
| CN | 111904666 A | * | 11/2020 | ............ G06T 17/00 |
| CN | 112386345 A | | 2/2021 | |
| WO | WO02087647 A1 | | 11/2002 | |
| WO | WO2011125760 A1 | | 10/2011 | |
| WO | WO2022100574 A1 | | 5/2022 | |

* cited by examiner

ALVEOLAR BONE AUGMENTATION SCAFFOLD SYSTEM

CROSS-REFERENCE TO RELATED APPLICATIONS

The present application claims priority to and is a bypass continuation-in-part application of PCT Application No. PCT/CN2021/129566, filed Nov. 9, 2021, which claims priority to the Chinese patent application with the filing no. CN 202011268945.3, filed Nov. 13, 2020, and entitled "Alveolar Bone Augmentation Scaffold System", the contents of each of which are incorporated herein by reference in entirety.

TECHNICAL FIELD

The present disclosure belongs to the medical field, and specifically, the present disclosure relates to a 3D-printed alveolar bone augmentation scaffold (support frame) system in the field of maxillofacial surgery.

BACKGROUND ART

In the existing alveolar bone augmentation procedure, bone substitute powder is usually used to fill alveolar defects for the horizontal or vertical augmentation, but the conventional bone substitute powder has the following drawbacks: 1. the cost is high; 2. it is hard to maintain the integrity of bone substitute filled area. Meanwhile, the bone substitute powder is likely to overflow from a sutured part to cause loss of the material when the bone substitute powder is subjected to unexpected extrusion after subsequent suturing, and finally the filling result is unsatisfied; 3. the height of the new alveolar bone formed is insufficient, and a filling area finally formed often cannot reach an expected height due to poor shape maintenance, insufficient support of force, and post-operative atrophy contributed to sutured surfaces, finally deteriorate the stability and aesthetic results; and 4. alveolar defects with complex geometry is hard to be addressed with bone substitute powder. And due to individual alveolar defects' differences, bone substitute powder is not an appropriate option for all patients in order to achieve best functional and cosmetic results.

In view of the above shortcomings, an improved technical method of 3D printing an alveolar bone augmentation scaffold system has been proposed now. By preparing alveolar bone augmentation scaffold with a porous structure by the 3D printing technology, the scaffolds with a specific structure can be perfectly fitted to different patients. However, for the existing 3D printing technology, the repair effect of the scaffold is usually improved by optimizing the material. The prepared alveolar bone scaffold can hardly match with the human alveolar bone growth, then the final repair effect is difficult to effectively control and the repair effect is not favorable.

Therefore, there is an urgent need in the art for an alveolar bone augmentation scaffold. This novel approach can effectively improve the geometrical and regenerative fit between the alveolar bone and the human bone tissue growth, so as to improve the bone tissue regeneration effect.

SUMMARY

An alveolar bone augmentation scaffold system, wherein the scaffold system includes the following structures:

a porous augmentation scaffold fabricated by 3D printing using composite materials for filling alveolar bone defects; and a mechanical separating plate, wrapped around the porous augmentation scaffold with a biomimetic structure for restoring alveolar bone defects;

the augmentation scaffold has a first region close to dental pulp, a second region away from the dental pulp, and a third region surrounding the second region, wherein the three-dimensional porous structures of the above three regions have pore diameters of R1, R2, and R3, respectively, where $R1 \geq R2 > R3$.

BRIEF DESCRIPTION OF DRAWINGS

In order to more clearly illustrate technical solutions of embodiments of the present disclosure, drawings which need to be used in the embodiments of the present disclosure will be introduced briefly below, and it should be understood that the drawings below merely show some embodiments of the present disclosure, therefore, they should not be considered as limitation on the scope, and those ordinarily skilled in the art still could obtain other relevant drawings according to these drawings, without using any creative effort.

ILLUSTRATION OF REFERENCE SIGNS

Figure 1:
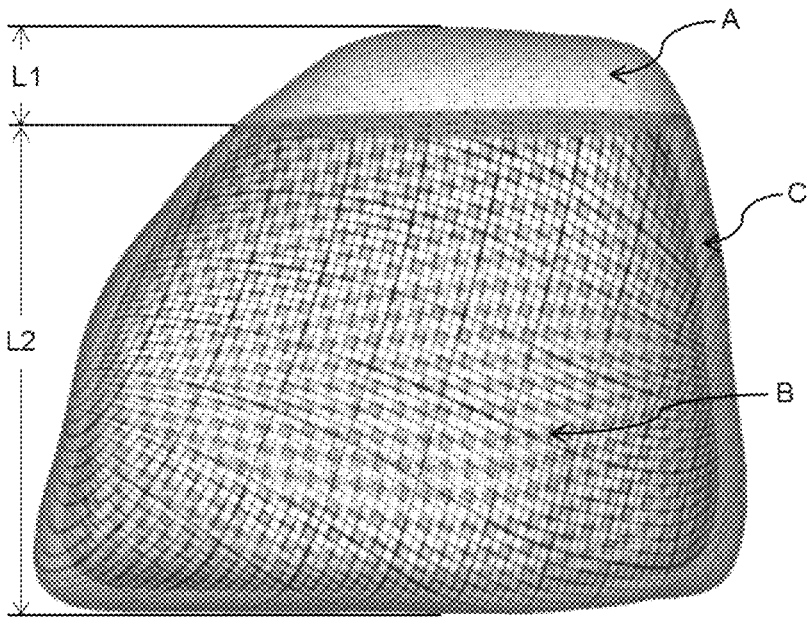
FIG. 1 is a perspective schematic view of an augmentation scaffold in the present disclosure.

A—first region in augmentation scaffold, B—second region in augmentation scaffold, C—third region in augmentation scaffold, 1—augmentation scaffold, 2—mechanical separating plate, 21—through-hole, 22—fixed wing, 3—shaping template.

DETAILED DESCRIPTION OF EMBODIMENTS

The technical solutions in the embodiments of the present disclosure will be described clearly and completely below with reference to the accompanying drawings in the embodiments of the present disclosure, and apparently, some but not all embodiments of the present disclosure are described. Generally, components in the embodiments of the present disclosure, as described and shown in the accompanying drawings herein, may be arranged and designed in various different configurations. Therefore, the detailed description below of the embodiments of the present disclosure provided in the accompanying drawings is not intended to limit the scope claimed in the present disclosure, but merely illustrates chosen embodiments of the present disclosure. All of other embodiments obtained by a person skilled in the art based on the embodiments of the present disclosure without creative efforts shall fall within the scope of protection of the present disclosure.

If no specific conditions are specified in the embodiments, they are carried out under normal conditions or conditions recommended by manufacturers. If manufacturers of reagents or apparatuses used are not specified, they are conventional products commercially available.

In the present disclosure, orientation or positional relationships indicated by terms such as "upper", "lower", "left", "right", "front", "rear", "top", "bottom", "inner", "outer", "middle", "vertical", "horizontal", "transverse", and "longitudinal" are based on orientation or positional relationships as shown in the accompanying drawings. These terms are mainly used to better describe the present disclosure and the embodiments thereof, and are not used to limit that the device, element, or component referred to must be in a specific orientation, or be constructed and operated in a specific orientation.

In addition, some of the above terms may be used to indicate other meanings in addition to the orientation or positional relationships, for example, the term "upper" also may be used to indicate a certain attachment relationship or connection relationship in some cases. For those ordinarily skilled in the art, specific meanings of these terms in the present disclosure could be understood according to specific circumstances.

Besides, terms "install (mount)", "provide (set)", "provided with", "connect", and "join" should be understood in a broad sense. For example, it may be a fixed connection, a detachable connection, or an integral configuration; it may be a mechanical connection, and also may be an electrical connection; it may be a direct connection, indirect connection through an intermediary, or inner communication between two devices, elements or components. For those ordinarily skilled in the art, specific meanings of the above-mentioned terms in the present disclosure could be understood according to specific circumstances.

Besides, terms such as "first" and "second" are mainly used to distinguish different devices, elements or components (specific types and configurations may be the same or different), rather than indicating or implying the relative importance or quantity of the device, element or component referred to. "Multiple (a plurality of)" means two or more, unless otherwise illustrated.

In order to solve the preceding problems existing in the prior art, the present disclosure provides an alveolar bone augmentation scaffold system, wherein a 3D-printed bone augmentation scaffold is used to fill an alveolar bone defect part, and a mechanical separating plate wrapped around the bone augmentation scaffold is used to provide a biomimetic structure for restoring an alveolar bone defect, which can effectively improve the bone tissue regeneration effect, and have a great application prospect in the dental and maxifacial fields.

Technical solutions of the present disclose are implemented as follows:

an alveolar bone augmentation scaffold system, wherein the scaffold system includes the following structures:

a porous augmentation scaffold fabricated by 3D printing using composite materials for filling alveolar bone defects;

a mechanical separating plate, wrapped around the porous augmentation scaffold with a biomimetic structure for restoring alveolar bone defects;

the augmentation scaffold has a first region close to dental pulp, a second region away from the dental pulp, and a third region surrounding the second region, wherein pore diameters of the three-dimensional porous structure of the above three regions are R1, R2, and R3, respectively, and they satisfy R1≥R2>R3.

In some embodiments, the R1, R2, and R3 satisfy R1>R2>R3.

In some embodiments, the pore diameter R1 of the first region is not less than 0.4 mm, the pore diameter R2 of the second region is 0.2 mm-0.5 mm, and the pore diameter R3 of the third region is not greater than 0.4 mm.

In some embodiments, the pore diameter R1 of the first region is 0.4 mm-0.6 mm, the pore diameter R2 of the second region is 0.3 mm-0.5 mm, and the pore diameter R3 of the third region is 0.2 mm-0.4 mm. In some embodiments, the pore diameter R1 of the first region is 0.5 mm, the pore diameter R2 of the second region is 0.4 mm, and the pore diameter R3 of the third region is 0.3 mm.

In some embodiments, pore channels of at least the first region and the second region are triangular pores, and the pore diameter is a diameter of an inscribed circle of a triangle.

In some embodiments, a ratio of a longitudinal extension length L1 of the first region to a longitudinal extension length L2 of the second region is L1:L2=1:3-1:8, and thickness of the third region is not greater than 1 mm.

In some embodiments, the ratio of the longitudinal extension length L1 of the first region to the longitudinal extension length L2 of the second region is L1:L2=1:4-1:6.5, for example, L1:L2=1:5, and thickness of the third region is not greater than 1 mm.

In some embodiments, the polymer material of the first region is PCL (polycaprolactone)-PLGA (polylactic-glycolic acid)-TCP (tricalcium phosphate), the polymer material of the second region is PCL-TCP, and the polymer material of the third region is PCL, wherein an average molecular weight Mn of the PCL in the first region and/or the second region is 1 w-5 w, and an average molecular weight Mn of the PCL in the third region is 5 w-10 w.

In some other embodiments, the polymer material of the first region is PCL-PLGA-TCP, the polymer materials of the second and third regions are PCL-TCP, wherein the average molecular weight Mn of the PCL in the first region and/or the second region is 1 w-5 w, and the average molecular weight Mn of the PCL in the third region is 5 w-10 w. In some embodiments, the first, second, and third regions contain an equal amount of TCP.

In some embodiments, pores of the three-dimensional porous structure of the augmentation scaffold are filled with a water absorbent osteoinductive material, including but not limited to sodium alginate, sodium methacrylated alginate, sodium thiolated alginate, gelatin, methacrylated gelatin, thiolated gelatin, hyaluronic acid, methacrylated hyaluronic acid, thiolated hyaluronic acid, collagen, methacrylated collagen, thiolated collagen, and fibrin.

In some embodiments, the water absorbent polymer material is formed to have a three-dimensional network structure by photo-crosslinking.

In some embodiments, the mechanical separating plate is made by 3D printing with a PCL-PLGA composite material, wherein the PCL has an average molecular weight Mn of 1 w-5 w.

In some embodiments, a mass ratio of the PLC to the PLGA in the PCL-PLGA composite material forming the mechanical separating plate is 1:(0.25-4) (1:0.25-1:4). For example, the mass ratio of the PCL to the PLGA in the PCL-PLGA composite material forming the mechanical separating plate is 1:1.

In some embodiments, the mechanical separating plate has a plurality of through-holes, and/or the mechanical separating plate has spreading wings on a side of scaffolds for fixation.

The implementation solutions of the present disclosure will be described in detail below with reference to accompanying drawings and embodiments, while a person skilled in the art would understand that the following embodiments are merely used for illustrating the present disclosure, but should not be considered as limitation on the scope of the present disclosure.

I. Study on Structure of Alveolar Bone Augmentation Scaffold System

Figure 3:
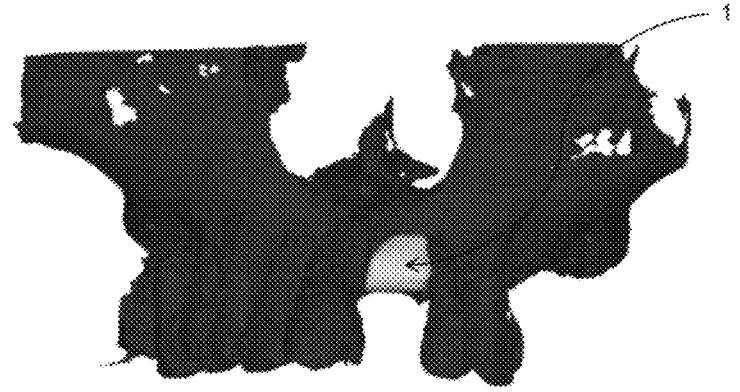
FIG. 3 is a perspective schematic view of filling an alveolar bone defect part with the augmentation scaffold in the present disclosure.
Figure 4:
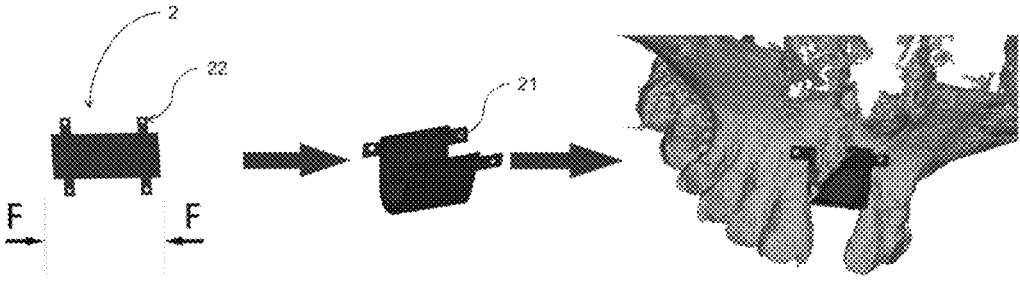
FIG. 4 is a schematic view of a process of repairing an alveolar bone when a mechanical separating plate in Embodiment 1 is used.
Figure 5:
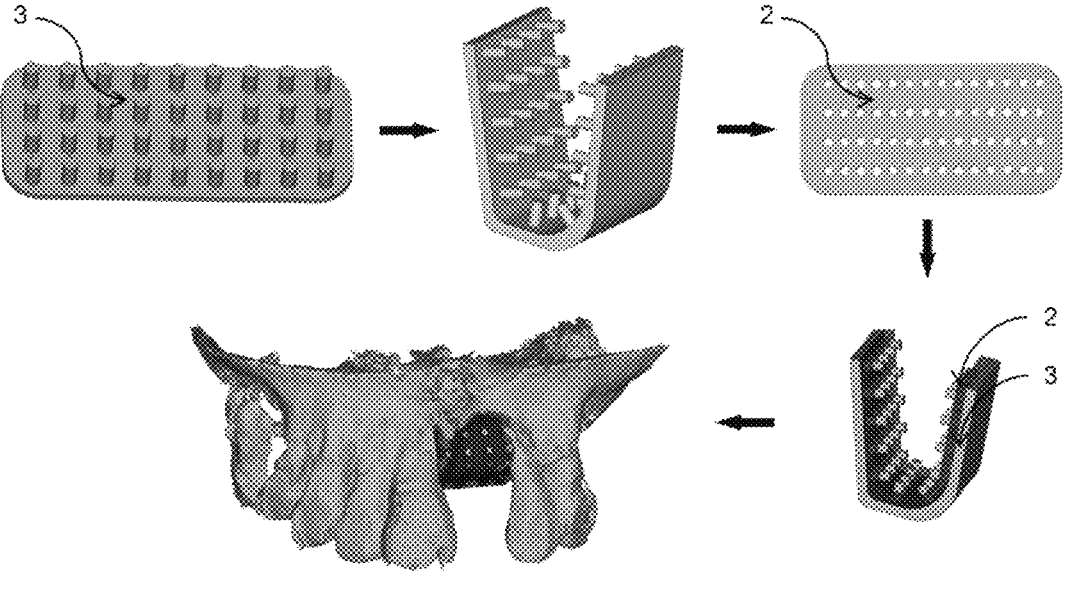
FIG. 5 is a schematic view of a process of repairing an alveolar bone when a mechanical separating plate in Embodiment 2 is used.

In the present embodiment, the alveolar bone augmentation scaffold system includes an augmentation scaffold 1 as shown in FIG. 1 and FIG. 3, and a mechanical separating plate 2 as shown in FIG. 4 and FIG. 5. In the above, the augmentation scaffold 1 is filled in an alveolar bone defect, and the mechanical separating plate is wrapped around the augmentation scaffold 1 and has a biomimetic structure for restoring an alveolar bone defect surface.

Specific structures of the augmentation scaffold 1 and the mechanical separating plate 2 in the present embodiment are respectively described in detail below.

(1) Augmentation Scaffold 1

As shown in FIG. 1, the augmentation scaffold 1 is formed by 3D printing a composite polymer material and has a three-dimensional porous structure, wherein according to relative positions filled in the alveolar bone, the augmentation scaffold 1 is divided into a first region A close to the dental pulp, a second region B away from the dental pulp, and a third region C surrounding the second region, wherein a pore diameter in the three-dimensional porous structure of the first region A is denoted by R1, a pore diameter in the three-dimensional porous structure of the second region B is denoted by R2, a pore diameter in the three-dimensional porous structure of the third region C is denoted by R3, and in the augmentation scaffold 1 having the three-dimensional porous structure, R1, R2, and R3 satisfy R1≥R2>R3 or R1>R2>R3. Based on individual requirements, the technical effect of guiding the blood of the dental pulp into the interior of the scaffold to improve the healing speed also can be obtained when R2 is close to the value of R1 in the 3D-printed alveolar bone, but when R1>R2, it may be more conducive to the distribution of blood, and the effect of improving the healing speed is more significant, therefore, R1>R2 is preferred. Moreover, when R2>R3, i.e., R3 is relatively smaller, effective control over stem cells and blood flow can be realized, ensuring that the stem cells, the blood, etc. in the bone tissues will not permeate to the outside of the scaffold and that the body fluid is effectively controlled in the bone growth area, thus realizing the controllable growth of the alveolar bone.

Figure 2:
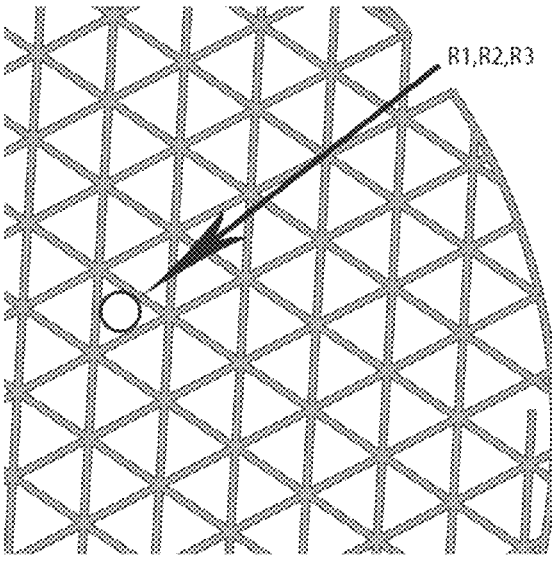
FIG. 2 is a structural schematic view of pore channels of the augmentation scaffold in the present disclosure.

As indicated by the arrow in FIG. 2, the pore diameter in the present disclosure refers to diameter of the largest inner circle in the cross section of the pore channel, wherein optionally, the pore channels of the first region A, the second region B, and the third region C all have a triangular structure as shown in FIG. 2, and for specific test results, reference can be made to the following Table 1.

By controlling the pore diameters inside the augmentation scaffold 1 to satisfy the specific distribution form in the above, the augmentation scaffold 1 with a relatively large pore diameter in the area of the dental pulp can promote the penetration of stem cells and blood in the dental pulp, and promote the alveolar bone regeneration, meanwhile, as the specific surface area is large, the scaffold in this region can degrade rapidly, and match the characteristics of large blood supply and quick osteogenesis in the dental pulp area, so that a degradation rate of the first region A of the augmentation scaffold 1 and the growth rate of the alveolar bone have a better match; the second region B away from the dental pulp is in a structure with a relatively small pore diameter, and compared with the first region, this structure has a relatively small specific surface area and degrades relatively slowly, which can match the characteristics of relatively smaller blood supply and slower osteogenesis in this region compared to the first region, further matching the bone growth rate in this region. That is to say, by controlling the pore diameters inside the augmentation scaffold 1 to satisfy the above specific distribution form, the degradation rate of the scaffold in various regions, no matter the first region A close to the dental pulp or the second region B away from the dental pulp, can be better matched with the bone growth rates of corresponding regions. The third region C surrounding the second region B, which is a dense structure with a relatively small pore diameter, effectively controls the stem cells and blood flow, ensures that the stem cells, blood, etc. in the bone tissues will not penetrate to the outside of the stem and that the body fluid is effectively controlled in the bone growth region, thus realizing the controllable growth of the alveolar bone.

In the present disclosure, optional composite materials of various regions of the augmentation scaffold 1 are as follows: (1) the first region uses a composite polymer material of PCL (average molecular weight Mn=2W):PLGA (ratio of PLA to PGA is 50:50):TCP=4:4:2 by mass. In the above, PLGA degrades faster and also has better biocompatibility, and in combination with PCL with low molecular weight and fast degradation rate, the growth rate of alveolar bone in the first region is just matched, meanwhile, TCP can also promote osteogenesis; (2) the second and third regions use composite polymer materials of PCL:TCP=8:2 by mass. In the above, optionally, the average molecular weight of PCL in the third region is larger than the average molecular weight of PCL in the second region. In the above, PCL denotes polycaprolactone, PLGA denotes polylactic acid PLA-glycolic acid PGA, and TCP denotes tricalcium phosphate.

Through extensive verification and improvement, the inventors optimized the longitudinal extension lengths of the first region and the second region. Based on the comprehensive consideration and study of distribution characteristics of dental pulp area of the human alveolar bone and complex factors of practical blood supply, absorption, and healing, when the ratio of the longitudinal extension length L1 of the first region A to the longitudinal extension length L2 of the second region B is L1:L2=1:3-1:8, the scaffold is well matched with the healing rate of the bone tissues, and can obviously improve the healing rate of the bone tissues. Moreover, when the ratio of the longitudinal extension length L1 of the first region to the longitudinal extension length L2 of the second region B is L1:L2=1:4-1:6.5, it can render a better bone tissue healing efficiency and is substantially matched with the bone tissue rate of conventional patients. For the specific clinical test results, reference can be made to the following Table 2. In the above, the longitudinal extension length refers to the shortest distance extending from the dental pulp area to a region away from the dental pulp area. In addition, in order to ensure that the third region C in the scaffold structure can effectively avoid the overflow of flowable bone tissues such as blood and stem cells at the alveolar bone defect part, optionally, the depth of the third region C is not greater than 1 mm. By controlling the depth of the third region and in combination with the small pore diameter structure of the third region, the bone tissues can be effectively controlled inside the scaffold, ensuring a benign environment for bone growth, and further promoting the bone tissue healing.

In order to further improve the absorption of fluidic interstitial fluid by the augmentation scaffold 1, and further promote the bone tissue healing, in the present disclosure, after the 3D-printed augmentation scaffold 1 is formed, a photo-crosslinkable polymerizable monomer is filled in the interior of the scaffold main body 1, and by irradiating the monomer-filled augmentation scaffold 1 with light, the polymeric monomer in the inner pore channels of the augmentation scaffold 1 is photo-crosslinked to form a three-dimensional network structure with higher water absorption, and the water absorbent polymer in the pore channels of the scaffold main body can effectively promote the absorption of high-concentration platelets and plasma, thus further improving the osteogenesis speed and accelerating the tissue healing.

(2) Mechanical Separating Plate 2

The mechanical separating plate 2 as shown in FIG. 4 can be formed by 3D printing a composite material with PCL (molecular weight Mn=2W):PLGA (the ratio of PLA to PGA is 50:50)=1:1 by mass according to a patient's defect surface and a biomimetic structure matched with the defect surface is formed. The above composite material has the technical effects of degrading quickly and providing sufficient mechanical support for the scaffold before the scaffold degrades. In order to further fix the above mechanical separating plate 2 outside the scaffold main body 1 so as to ensure the effectiveness of the support, in the present disclosure, the mechanical separating plate 2 is provided with through-holes 21, and the through-holes 21 are sized to match degradable screws, so as to facilitate nailing and fixation.

As shown in FIG. 4, under the action of a bending force F, the mechanical separating plate 2 is bent from a planar configuration to a bending configuration matched with the shape of the alveolar bone. In order to fix the mechanical separating plate 2 and the alveolar bone more stably, fixed wings 22 protruding from the side are formed on at least one side of the mechanical separating plate 2, the through-holes 21 are provided on the fixed wings 22, and the fixed wings 22 are further fixed on an outer surface of the alveolar bone by means of screws, thus an effective contact area between the mechanical separating plate and the alveolar bone is extended, and the support function of the mechanical separating plate to the internal augmentation scaffold is further improved.

In the present disclosure, the augmentation scaffold 1 cooperates with the mechanical separating plate 2 to form an augmentation scaffold system. On one hand, the augmentation scaffold 1 located at the bone tissue defect part can be effectively matched with the bone tissue growth and promote the tissue healing, and on the other hand, by suturing the mechanical separating plate 2 wrapped around the augmentation scaffold 1, a support and protective effect can be formed to the scaffold main body 1, which not only ensures that the scaffold main body is tightly attached to the bone tissues to promote growth, but also meanwhile can prevent damage to the tissues at the treatment site by foreign objects while eating, and thus avoid secondary injury.

As an alternative mode of preparing the mechanical separating plate in Embodiment 1, a shaping template 3 is used in the present embodiment to assist the shaping of the mechanical separating plate 2. Specifically, as shown in FIG. 5, in the present embodiment, first, the shaping template 3 is prepared, wherein a surface of the shaping template 3 has uniformly arranged protrusions, and correspondingly, the through-holes on the mechanical separating plate 2 are matched with these protrusions. In the process of preparing the mechanical separating plate 2 having a bending configuration, the shaping template 3 is first bent to a bending configuration matched with the alveolar bone defect surface, subsequently, the mechanical separating plate 2 to be shaped is placed on an inner side of the bent shaping template 3, and the protrusions on the shaping template are made to penetrate into the through-holes on the mechanical separating plate 2 to further position the mechanical separating plate 2, after that, the mechanical separating plate 2 fixed on the shaping template 3 is placed in warm water, and under the action of heat, the mechanical separating plate 2 is remodeled into a bent configuration identical to that of the shaping template 3 and shaped. In the present embodiment, by using the bendable metal shaping template 3, the mechanical separating plate 2 is allowed to obtain a bionic configuration matched with the alveolar bone defect surface. Finally, the shaped mechanical separating plate 2 is made to cover the alveolar bone defect surface and is fixed, and eventually, the mechanical fixation and support of the augmentation scaffold 1 pre-filled in the alveolar bone are completed.

II. Study on Pore Diameters and Structures of Various Regions of the Augmentation Scaffold 1

In order to further improve the effective control over the tissue growth, the present disclosure optimizes the pore diameter size and form in different regions of the scaffold, so as to achieve the technical effect of improving the bone tissue growth. The augmentation scaffold main bodies 1 of different pore diameters, structures and sizes are applied to beagle alveolar bone defects for testing, and data as shown in the following Table 1 is obtained. In the above, the bone tissue healing condition is judged by X-ray imaging, bone fusion of the scaffold is taken as a judgment criterion for bone tissue healing, and due to individual differences, the number of healing days is a statistical reference range, and data collection samples in the comparative examples and test examples are no less than 20 cases. As a specific embodiment, in the augmentation scaffold main bodies used in Test Examples 2-6 of this test, the longitudinal extension length L1 of the first region A is 1.5 mm, and the longitudinal extension length L2 of the second region B is 7.5 mm.

TABLE 1

| | Comparative Example | Test Example 1 | Test Example 2 | Test Example 3 | Test Example 4 | Test Example 5 | Test Example 6 |
|---|---|---|---|---|---|---|---|
| | Conventional 3D-printed PCL-PLGA scaffold | R1 = 0.5 mm R2 = 0.4 mm R3 = 0.3 mm The first and second regions are irregularly-shaped pores | R1 = 0.5 mm R2 = 0.4 mm R3 = 0.3 mm The first and second regions are nearly circular pores | R1 = 0.5 mm R2 = 0.4 mm R3 = 0.3 mm The first and second regions are triangular pores | R1 = 0.6 mm R2 = 0.5 mm R3 = 0.4 mm The first and second regions are triangular pores | R1 = 0.4 mm R2 = 0.3 mm R3 = 0.2 mm The first and second regions are triangular pores | R1 = 0.5 mm R2 = 0.5 mm R3 = 0.3 mm The first and second regions are triangular pores |
| Bone tissue healing time | 320-360 days | 210-240 days | 200-220 days | 160-180 days | 170-190 days | 180-200 days | 180-200 days |

It can be seen from the above table that the pore structures and sizes in different scaffold main bodies directly determine the bone tissue healing time of the alveolar bones. By comparing Test Examples 1-3, it can be seen that the shape of the pore diameter also influences the healing speed of the bone tissues. On the basis of the numerical values of R1-R3 selected in the present disclosure, the healing effect of the triangular pores (a cross section of the pore channel is of an approximately triangular structure) is the best, the healing time of the bone tissues can be shortened to less than ½ of that of the conventional 3D-printed scaffold, thus greatly shortening the healing time, reducing the overall treatment time of alveolar bone augmentation procedure, and decreasing the treatment time of the patient. Meanwhile, it can be seen from Test Examples 3-6 that within the numerical ranges of R1-R3 selected in the present disclosure, the healing time can be greatly shortened.

The influence of the scaffold on the bone tissue healing is observed when the longitudinal extension lengths L1 and L2 of the first region and the second region in the scaffold are different, wherein other parameters are the same as those in Test Example 3 except that the lengths L1 and L2 are changed. Specific study results are as shown in Table 2.

TABLE 2

| | Comparative Example Conventional 3D-printed PCL-PLGA scaffold | Test Example 3 | Test Example 7 | Test Example 8 | Test Example 9 |
|---|---|---|---|---|---|
| | | L1 = 1.5 mm L2 = 7.5 mm | L1 = 1 mm L2 = 8 mm | L1 = 2 mm L2 = 6 mm | L1 = 1.2 mm L2 = 7.8 mm |
| Bone tissue healing time | 320-360 days | 160-180 days | 180-200 days | 170-200 days | 170-190 days |

It can be seen from the above table that the longitudinal extension lengths L1 and L2 of the first region and the second region have certain influence on the bone tissue healing effect, wherein when the numerical value of L1:L2 falls within the range of 1:4-1:6.5 in Test Examples 3 and 9, the bone tissue healing time is slightly shorter than that in Test Examples 7 and 8, thus it can be seen that when the ratio of L1 to L2 is too large or too small, the bone tissue healing effect will be affected.

The technical solutions of the present disclose have the following advantages.

1. The 3D-printed alveolar bone augmentation scaffold system provided in the present disclosure completely restores the patient's alveolar bone defect by a medical image modeling method, and then the scaffold is made by 3D printing, wherein the material cost is low, the form is well maintained, the formation height of the alveolar bone is controllable, and the advantage of individualizing the patient's alveolar bone augmentation is provided. Compared with the conventional 3D-printed scaffold, the inventors of the present disclosure have found that by optimizing the pore channel structures of the alveolar bone augmentation scaffold, such as the pore diameter size and the pore shape, according to the bone growth situation and blood supply of different dental bone sites, etc., the alveolar bone growth can be effectively improved, and the controllability of bone growth is effectively promoted, thus greatly improving the alveolar bone repairing effect.

2. By providing the alveolar bone augmentation scaffold with the mechanical separating plate having the biomimetic structure and attached to the alveolar defect surface, on one hand, the stability of the augmentation scaffold is improved, so that the scaffold main body is in firm contact with bone tissues, and the promoting effect of the augmentation scaffold on the bone tissue healing and growth is improved and ensured; and on the other hand, the mechanical separating plate also can achieve the effect of shaping the profile of the alveolar bone, ensure the height of the new alveolar bone formed to reach an expected effect, and improve the stability of implanted tooth and the shaping effect of the alveolar bone.

Finally, it should be explained that various embodiments and test examples above are merely used to illustrate the technical solutions of the present disclosure, rather than limiting the present disclosure; although the detailed description is made to the present disclosure with reference to various preceding embodiments, those ordinarily skilled in the art should understand that they still could modify the technical solutions recited in various preceding embodiments, or make equivalent substitutions to some or all of the technical features therein; and these modifications or substitutions do not make the corresponding technical solutions essentially depart from the scope of the technical solutions of various embodiments of the present disclosure.

INDUSTRIAL APPLICABILITY

The alveolar bone augmentation scaffold system of the present disclosure, by filling the alveolar bone defect with the 3D-printed bone augmentation scaffold and providing the biomimetic structure for restoring the alveolar bone defect with the mechanical separating plate wrapped around the bone augmentation scaffold, can effectively improve the bone tissue regeneration effect, and thus have a great application prospect in the dental and maxifacial fields.

What is claimed is:

1. An alveolar bone augmentation scaffold system, wherein the scaffold system comprises following structures:
   a porous augmentation scaffold fabricated by 3D printing using composite materials for filling alveolar bone defects; and
   a mechanical separating plate, wrapped around the porous augmentation scaffold with a biomimetic structure for restoring alveolar bone defects,
   wherein
   the augmentation scaffold has a first region configured to be close to dental pulp, a second region configured to be away from the dental pulp, and a third region surrounding the second region, wherein pore diameters of the three-dimensional porous structure of the above three regions are R1, R2, and R3, respectively, and they satisfy R1>R2>R3,
   wherein a polymer material of the first region is PCL-PLGA-TCP, a polymer material of the second region is PCL-TCP, and a polymer material of the third region is PCL, wherein a number-average molecular weight of the PCL in the first region and/or the second region is $1 \times 10^4$ Da-$5 \times 10^4$ Da, and a number-average molecular weight of the PCL in the third region is $5 \times 10^4$ Da-$10 \times 10^4$ Da.

2. The alveolar bone augmentation scaffold system according to claim 1, wherein R1, R2, and R3 satisfy R1>R2>R3.

3. The alveolar bone augmentation scaffold system according to claim 1, wherein the pore diameter R1 of the first region is not less than 0.4 mm, the pore diameter R2 of the second region is 0.2 mm-0.5 mm, and the pore diameter R3 of the third region is not greater than 0.4 mm.

4. The alveolar bone augmentation scaffold system according to claim 3, wherein the pore diameter R1 of the first region is 0.4 mm-0.6 mm, the pore diameter R2 of the second region is 0.3 mm-0.5 mm, and the pore diameter R3 of the third region is 0.2 mm-0.4 mm.

5. The alveolar bone augmentation scaffold system according to claim 4, wherein the pore diameter R1 of the first region is 0.5 mm, the pore diameter R2 of the second region is 0.4 mm, and the pore diameter R3 of the third region is 0.3 mm.

6. The alveolar bone augmentation scaffold system according to claim 1, wherein pore channels of at least the first region and the second region are triangular pores, and the pore diameter is a diameter of an inscribed circle of a triangle.

7. The alveolar bone augmentation scaffold system according to claim 1, wherein a ratio of a longitudinal extension length L1 of the first region to a longitudinal extension length L2 of the second region is L1:L2=1:3-1:8, and a thickness of the third region is not greater than 1 mm.

8. The alveolar bone augmentation scaffold system according to claim 7, wherein the ratio of the longitudinal extension length L1 of the first region to the longitudinal extension length L2 of the second region is L1:L2=1:4-1: 6.5, and the thickness of the third region is not greater than 1 mm.

9. The alveolar bone augmentation scaffold system according to claim 8, wherein the ratio of the longitudinal extension length L1 of the first region to the longitudinal extension length L2 of the second region is L1:L2=1:5.

10. The alveolar bone augmentation scaffold system according to claim 1, wherein voids of the three-dimensional porous structure of the augmentation scaffold are filled with a water absorbent osteoinductive material selected from the group consisting of sodium alginate, sodium methacrylated alginate, sodium thiolated alginate, gelatin, methacrylated gelatin, thiolated gelatin, hyaluronic acid, methacrylated hyaluronic acid, thiolated hyaluronic acid, collagen, methacrylated collagen, thiolated collagen, and fibrin.

11. The alveolar bone augmentation scaffold system according to claim 10, wherein a three-dimensional network structure is formed by photo-crosslinking using the water absorbent osteoinductive material.

12. The alveolar bone augmentation scaffold system according to claim 1, wherein the mechanical separating plate is made by 3D printing with a PCL-PLGA composite material, and wherein the PCL has a number-average molecular weight of $1 \times 10^4$ Da-$5 \times 10^4$ Da.

13. The alveolar bone augmentation scaffold system according to claim 12, wherein a mass ratio of the PCL to the PLGA in the PCL-PLGA composite material forming the mechanical separating plate is 1:0.25-1:4.

14. The alveolar bone augmentation scaffold system according to claim 13, wherein the mass ratio of the PCL to the PLGA in the PCL-PLGA composite material forming the mechanical separating plate is 1:1.

15. The alveolar bone augmentation scaffold system according to claim 12, wherein the mechanical separating plate has a plurality of through-holes, and/or the mechanical separating plate has spreading wings on a side of scaffolds for fixation.

16. The alveolar bone augmentation scaffold system according to claim 12, wherein in the PCL-PLGA, a ratio of PLA to PGA in the PLGA is 50:50.

17. The alveolar bone augmentation scaffold system according to claim 14, wherein in the polymer material PCL-PLGA-TCP of the first region, a ratio of PLA to PGA in the PLGA is 50:50.

18. An alveolar bone augmentation scaffold system, wherein the scaffold system comprises following structures:

a porous augmentation scaffold fabricated by 3D printing using composite materials for filling alveolar bone defects; and a mechanical separating plate, wrapped around the porous augmentation scaffold with a biomimetic structure for restoring alveolar bone defects, wherein the augmentation scaffold has a first region configured to be close to dental pulp, a second region configured to be away from the dental pulp, and a third region surrounding the second region, wherein pore diameters of the three-dimensional porous structure of the above three regions are R1, R2, and R3, respectively, and they satisfy R1>R2>R3, wherein a polymer material of the first region is PCL-PLGA-TCP, polymer materials of the second and third regions are PCL-TCP, wherein a number-average molecular weight of the PCL in the first region and/or the second region is $1 \times 10^4$ Da-$5 \times 10^4$ Da, and a number-average molecular weight of the PCL in the third region is $5 \times 10^4$ Da-$10 \times 10^4$ Da.

19. The alveolar bone augmentation scaffold system according to claim 18, wherein the first, second, and third regions contain an equal amount of TCP.

* * * * *